United States Patent
Rao et al.

(10) Patent No.: US 11,060,076 B2
(45) Date of Patent: Jul. 13, 2021

(54) METHOD FOR PRODUCING 1,2-AMINO ALCOHOL COMPOUND BY WHOLE CELL TRANSFORMATION

(71) Applicant: JIANGNAN UNIVERSITY, Jiangsu (CN)

(72) Inventors: Zhiming Rao, Jiangsu (CN); Song Liu, Jiangsu (CN); Renjie Gao, Jiangsu (CN); Xian Zhang, Jiangsu (CN); Taowei Yang, Jiangsu (CN); Meijuan Xu, Jiangsu (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 0 days.

(21) Appl. No.: 16/682,486

(22) Filed: Nov. 13, 2019

(65) Prior Publication Data

US 2020/0149077 A1    May 14, 2020

(30) Foreign Application Priority Data

Nov. 13, 2018    (CN) .......................... 201811344825.X

(51) Int. Cl.
| | | |
|---|---|---|
| C12N 9/14 | (2006.01) | |
| C12N 9/04 | (2006.01) | |
| C12N 9/10 | (2006.01) | |
| C12N 9/02 | (2006.01) | |
| C12N 15/00 | (2006.01) | |
| C12N 1/20 | (2006.01) | |
| C12P 13/00 | (2006.01) | |
| C12P 7/04 | (2006.01) | |
| C12N 9/06 | (2006.01) | |

(52) U.S. Cl.
CPC .............. *C12N 9/14* (2013.01); *C12N 9/0006* (2013.01); *C12N 9/0016* (2013.01); *C12N 9/1096* (2013.01); *C12P 13/001* (2013.01); *C12Y 101/01001* (2013.01); *C12Y 104/01002* (2013.01); *C12Y 303/0201* (2013.01)

(58) Field of Classification Search
CPC ...... C12N 9/14; C12N 9/1096; C12N 9/0006; C12N 9/0016; C12P 13/00; C12P 7/04
See application file for complete search history.

(56) References Cited

U.S. PATENT DOCUMENTS

2017/0067084 A1* 3/2017 Li ........................ C12N 9/0069

OTHER PUBLICATIONS

CP006936.2. GenBank Database, 2014.*
Q9I6J2_PSEAE. UniProtKB/TrEMBL Database. Jun. 7, 2017.*
Wu. Highly regio- and enantioselective multiple oxy- and amino-functionalizations of alkenes by modular cascade biocatalysis. Nat Commun. Jun. 14, 2016;7:11917.*

* cited by examiner

*Primary Examiner* — Yong D Pak
(74) *Attorney, Agent, or Firm* — Dinsmore & Shohl LLP

(57) ABSTRACT

The present invention discloses a method for producing a 1,2-amino alcohol compound by utilizing whole-cell transformation, and belongs to the technical field of gene engineering and microorganism engineering. According to the present invention, engineered *Escherichia coli* co-expresses epoxide hydrolase, alcohol dehydrogenase, ω-transaminase and glutamate dehydrogenase, is capable of realizing whole-cell catalysis of an epoxide in one step to synthesize a 1,2-amino alcohol compound, and meanwhile, can realize regeneration of coenzyme $NADP^+$ and an amino donor L-Glu; alcohol dehydrogenase expressed by the engineered *Escherichia coli* is RBS optimized alcohol dehydrogenase, and such RBS optimization can control the expression quantity of alcohol dehydrogenase, so that the catalysis rate of alcohol dehydrogenase and transaminase can achieve an optimum ratio, to eliminate influence caused by a rate-limiting step in a catalyzing course.

4 Claims, No Drawings
Specification includes a Sequence Listing.

SEQUENCE LISTING

<160> NUMBER OF SEQ ID NOS: 36

<210> SEQ ID NO 1
<211> LENGTH: 1143
<212> TYPE: DNA
<213> ORGANISM: Artificial sequence
<220> FEATURE:
<223> OTHER INFORMATION: a gene encoding the epoxide hydrolase (SpEH)

<400> SEQUENCE: 1

```
atgaacgtcg aacatatccg cccgttccgc gtcgaggtgc cgcaggacgc gctcgacgat      60
cttcgcgacc ggctggcgcg cactcgctgg cccgagaagg aaacggtcga cgactgggat     120
cagggcatcc cgctcgccta tgcccgcgaa ctcgccatct actggcgcga cgagtacgac     180
tggcggcgga tcgaggcgcg gctcaacacc tggcccaact ttctggccac agtcgacggg     240
ctcgatatcc atttcctcca tatccgctcg gacaatcctg ccgcgcggcc gctggtgttg     300
acgcacggct ggccgggatc ggtcctcgaa tttctcgacg tcatcgaacc gctgtcggcc     360
gactatcacc tcgtcatccc gtcgcttccc ggtttcggtt tctcgggcaa gcccaccgc      420 cccggctggg atgtcgagca tatcgccgcc gcgtgggacg cgctgatgcg cgcgctcggc     480
tatgaccgct attttgcgca gggcggcgac tggggcagcg cggtaacctc ggcgatcggc     540
atgcaccacg ccggccattg cgcgggcatc cacgtcaaca tggtcgtcgg cgcgccgccg     600
cccgagttga tgaacgacct caccgacgaa gagaagctct atctcgcgcg cttcggctgg     660
tatcaggcga aggacaatgg ctattcgacg cagcaggcga cgcggccgca gacgatcggc     720
tatgcgctca ccgattcccc ggccggacag atggcgtgga tcgcggagaa attccacggc     780
tggaccgatt gcgggcacca gcccggcggc cagtcggtcg gcggccaccc cgaacaggcg     840
gtctcgaagg atgcgatgct cgacacgatc agcctctatt ggctgaccgc cagcgccgct     900
tcgtcggcgc ggctatactg gcacagcttc cgtcagttcg cggcgggcga gatcgacgtg     960
ccgacgggat gcagcctgtt cccgaacgag atcatgcgcc tgtcgcggcg ctgggccgaa    1020
cggcggtatc gcaacatcgt ctattggagc gaagcggctc gcggcggcca tttcgccgcc    1080
tgggaacaac ccgagctgtt tgccgccgag gtccgcgcgg cctttgcaca gatggatctt    1140
tga                                                                  1143
```

<210> SEQ ID NO 2
<211> LENGTH: 1047
<212> TYPE: DNA
<213> ORGANISM: Artificial sequence
<220> FEATURE:
<223> OTHER INFORMATION: a gene encoding alcohol dehydrogenase (MnADH)

<400> SEQUENCE: 2

```
ctagatcgtg gcggtgtcga tcacgaaccg gtaccgcaca tcgctggaga gcacgcggtc      60
ccaggcctcg ttgacgtagg acgcctcgat gacctcgatc tccggggtga cgccgtgttc     120
ggcgcagaaa tcgagcatct cctgggtctc cgggataccg ccgatcatcg agccggagat     180
gctgcgtcgg ccacctgcca gcgggaagaa gggcacctcg agcggatgct cgggcgctcc     240
cagctcgacc agcgtgccat cgatcttgag cagcgagagg tactgaccga gatcgagatt     300
ggccgatacg tgttcagga tcagatcgaa cttgccggcc agcttgctga aggtgtcggg      360
atcgctggtc gcgtagtact cgtcggcgcc gagtcgcagg ccgtcttcca tcttcttgag     420
cgactggctg agaacggtca ccttggcgcc catcgcgtgg gccagcttga cgcccatgtg     480
gccgaggccg ccgagtccga cgattgcgac ctccttgccg gggccggcgt tccagtgctt     540
cagcggggag aacagcgtga tgcccgcgca cagcagggga gcggccttgt ccagcggaat     600
gctgtccggg atgcgcagga cgaacttttc gtcgacgacg atggcctggc tgtacccacc     660
ctgggtgatg gtgccgtccc ggtcggtggc ccgtaggtg ccgatcatgc cggtgcccag      720
gcagtactgc tccaggcccg ccgcgcagtt ctcgcagttc tggcaggagt tcaccatgca     780
gccgacgccg acgtggtcgc cgaccttgta cttggtgacc tccgagccga cctcggtgac     840
gacgccggcg atctcgtgac cgacgacgag cgggtagctg ggggtgcccc actcggcctt     900
ggcggtgtgg atgtcgctgt gacagatgcc ggcgaacttg atgtcgaagg ccacatcgtg     960
cgggccgacg tcacgcgcgt cgatggtggt cttggccagc ggatctgtcg cggaggtggc    1020
ggcgtaggcg gaaacggttg tggtcat                                         1047
```

<210> SEQ ID NO 3
<211> LENGTH: 456
<212> TYPE: PRT
<213> ORGANISM: Artificial sequence
<220> FEATURE:
<223> OTHER INFORMATION: an amino acid sequence of the
      omega-transaminase (PAKomega-TA)

<400> SEQUENCE: 3

```
Met Asn Ser Gln Ile Thr Asn Ala Lys Thr Arg Glu Trp Gln Ala Leu
1               5                   10                  15

Ser Arg Asp His His Leu Pro Pro Phe Thr Asp Tyr Lys Gln Leu Asn
            20                  25                  30

Glu Lys Gly Ala Arg Ile Ile Thr Lys Ala Glu Gly Val Tyr Ile Trp
        35                  40                  45

Asp Ser Glu Gly Asn Lys Ile Leu Asp Ala Met Ala Gly Leu Trp Cys
    50                  55                  60

Val Asn Val Gly Tyr Gly Arg Glu Glu Leu Val Gln Ala Ala Thr Arg
65                  70                  75                  80

Gln Met Arg Glu Leu Pro Phe Tyr Asn Leu Phe Phe Gln Thr Ala His
                85                  90                  95

Pro Pro Val Val Glu Leu Ala Lys Ala Ile Ala Asp Val Ala Pro Glu
            100                 105                 110

Gly Met Asn His Val Phe Phe Thr Gly Ser Gly Ser Glu Ala Asn Asp
        115                 120                 125

Thr Val Leu Arg Met Val Arg His Tyr Trp Ala Thr Lys Gly Gln Pro
    130                 135                 140

Gln Lys Lys Val Val Ile Gly Arg Trp Asn Gly Tyr His Gly Ser Thr
145                 150                 155                 160

Val Ala Gly Val Ser Leu Gly Gly Met Lys Ala Leu His Glu Gln Gly
                165                 170                 175
```

Asp Phe Pro Ile Pro Gly Ile Val His Ile Ala Gln Pro Tyr Trp Tyr
            180                 185                 190

Gly Glu Gly Gly Asp Met Ser Pro Asp Glu Phe Gly Val Trp Ala Ala
        195                 200                 205

Glu Gln Leu Glu Lys Lys Ile Leu Glu Val Gly Glu Glu Asn Val Ala
    210                 215                 220

Ala Phe Ile Ala Glu Pro Ile Gln Gly Ala Gly Gly Val Ile Val Pro
225                 230                 235                 240

Pro Asp Thr Tyr Trp Pro Lys Ile Arg Glu Ile Leu Ala Lys Tyr Asp
                245                 250                 255

Ile Leu Phe Ile Ala Asp Glu Val Ile Cys Gly Phe Gly Arg Thr Gly
            260                 265                 270

Glu Trp Phe Gly Ser Gln Tyr Tyr Gly Asn Ala Pro Asp Leu Met Pro
        275                 280                 285

Ile Ala Lys Gly Leu Thr Ser Gly Tyr Ile Pro Met Gly Gly Val Val
    290                 295                 300

Val Arg Asp Glu Ile Val Glu Val Leu Asn Gln Gly Gly Glu Phe Tyr
305                 310                 315                 320

His Gly Phe Thr Tyr Ser Gly His Pro Val Ala Ala Val Ala Leu
                325                 330                 335

Glu Asn Ile Arg Ile Leu Arg Glu Glu Lys Ile Ile Glu Lys Val Lys
            340                 345                 350

Ala Glu Thr Ala Pro Tyr Leu Gln Lys Arg Trp Gln Glu Leu Ala Asp
        355                 360                 365

His Pro Leu Val Gly Glu Ala Arg Gly Val Gly Met Val Ala Ala Leu
    370                 375                 380

Glu Leu Val Lys Asn Lys Lys Thr Arg Glu Arg Phe Thr Asp Lys Gly
385                 390                 395                 400

Val Gly Met Leu Cys Arg Glu His Cys Phe Arg Asn Gly Leu Ile Met
                405                 410                 415

Arg Ala Val Gly Asp Thr Met Ile Ile Ser Pro Pro Leu Val Ile Asp
            420                 425                 430

Pro Ser Gln Ile Asp Glu Leu Ile Thr Leu Ala Arg Lys Cys Leu Asp
        435                 440                 445

Gln Thr Ala Ala Ala Val Leu Ala
    450                 455

<210> SEQ ID NO 4
<211> LENGTH: 1139
<212> TYPE: DNA
<213> ORGANISM: Artificial sequence
<220> FEATURE:
<223> OTHER INFORMATION: RBS sequence

<400> SEQUENCE: 4
gctctagagg gaggagcaac tcccctaccc tacgctcatt ttcatgacca caaccgtttc      60
cgcctagatc gtggcggtgt cgatcacgaa ccggtaccgc acatcgctgg agagcacgcg     120
gtcccaggcc tcgttgacgt aggacgcctc gatgacctcg atctccgggg tgacgccgtg     180
ttcggcgcag aaatcgagca tctcctgggt ctccgggata ccgccgatca tcgagccgga     240
gatgctgcgt cggccaccct gccagcggga agagggcacc tcgagcggat gctcgggcgc     300
tcccagctcg accagcgtgc catcgatctt gagcagcgag aggtactgac cgagatcgag     360
attggccgat acggtgttca ggatcagatc gaacttgccg gccagcttgc tgaaggtgtc     420

```
gggatcgctg gtcgcgtagt actcgtcggc gccgagtcgc aggccgtctt ccatcttctt    480
gagcgactgg ctgagaacgg tcaccttggc gcccatcgcg tgggccagct tgacgcccat    540
gtggccgagg ccgccgagtc cgacgattgc gacctccttg ccggggccgg cgttccagtg    600
cttcagcggg gagaacagcg tgatgcccgc gcacagcagg ggagcggcct tgtccagcgg    660
aatgctgtcc gggatgcgca ggacgaactt ttcgtcgacg acgatggcct ggctgtaccc    720
accctgggtg atggtgccgt cccggtcggt ggcgccgtag gtgccgatca tgccggtgcc    780
caggcagtac tgctccaggc ccgccgcgca gttctcgcag ttctggcagg agttcaccat    840
gcagccgacg ccgacgtggt cgccgacctt gtacttggtg acctccgagc cgacctcggt    900
gacgacgccg gcgatctcgt gaccgacgac gagcgggtag ctgggggtgc cccactcggc    960
cttggcggtg tggatgtcgc tgtgacagat gccggcgaac ttgatgtcga aggccacatc   1020
gtgcgggccg acgtcacggc gctcgatggt ggtcttggcc agcggatctg tcgcggaggt   1080
ggcggcgtag gcggaaacgg ttgtggtcat cccaagcttc tagatcgtgg cggtgtcga   1139

<210> SEQ ID NO 5
<211> LENGTH: 1344
<212> TYPE: DNA
<213> ORGANISM: Artificial sequence
<220> FEATURE:
<223> OTHER INFORMATION: a gene encoding glutamate dehydrogenase (GluDH)

<400> SEQUENCE: 5
atggatcaga catattctct ggagtcattc ctcaaccatg tccaaaagcg cgacccgaat     60
caaaccgagt tcgcgcaagc cgttcgtgaa gtaatgacca cactctggcc ttttcttgaa    120
caaaatccaa aatatcgcca gatgtcatta ctggagcgtc tggttgaacc ggagcgcgtg    180
atccagtttc gcgtggtatg ggttgatgat cgcaaccaga tacaggtcaa ccgtgcatgg    240
cgtgtgcagt tcagctctgc catcggcccg tacaaaggcg tatgcgctt ccatccgtca     300 gttaaccttt ccattctcaa attcctcggc tttgaacaaa ccttcaaaaa tgccctgact    360
actctgccga tgggcggtgg taaaggcggc agcgatttcg atccgaaagg aaaaagcgaa    420
ggtgaagtga tgcgtttttg ccaggcgctg atgactgaac tgtatcgcca cctgggcgcg    480
gataccgacg ttccggcagg tgatatcggg gttggtggtc gtgaagtcgg ctttatggcg    540
gggatgatga aaagctctc caacaatacc gcctgcgtct tcaccggtaa gggccttttca    600 tttggcggca gtcttattcg cccggaagct accggctacg gtctggttta tttcacagaa    660
gcaatgctaa aacgccacgg tatgggtttt gaagggatgc gcgtttccgt ttctggctcc    720
ggcaacgtcg cccagtacgc tatcgaaaaa gcgatggaat ttggtgctcg tgtgatcact    780
gcgtcagact ccagcggcac tgtagttgat gaaagcggat tcacgaaaga gaaactggca    840
cgtcttatcg aaatcaaagc cagccgcgat ggtcgagtgg cagattacgc caaagaattt    900
ggtctggtct atctcgaagg ccaacagccg tggtctctac cggttgatat cgccctgcct    960
tgcgccaccc agaatgaact ggatgttgac gccgcgcatc agcttatcgc taatggcgtt   1020
aaagccgtcg ccgaaggggc aaatatgccg accaccatcg aagcgactga actgttccag   1080
caggcaggcg tactatttgc accgggtaaa gcggctaatg ctggtggcgt cgctacatcg   1140
ggcctggaaa tggcacaaaa cgctgcgcgc ctgggctgga aagccgagaa agttgacgca   1200
cgtttgcatc acatcatgct ggatatccac catgcctgtg ttgagcatgg tgtgaaggt    1260 gagcaaacca actacgtgca gggcgcgaac attgccggtt ttgtgaaggt tgccgatgcg   1320
atgctggcgc agggtgtgat ttaa                                          1344
```

<210> SEQ ID NO 6
<211> LENGTH: 30
<212> TYPE: DNA
<213> ORGANISM: Artificial sequence
<220> FEATURE:
<223> OTHER INFORMATION: primers P1 of epoxide hydrolase SpEH

<400> SEQUENCE: 6
cgggatccat gaacgttgaa cacatccgtc                                    30

<210> SEQ ID NO 7
<211> LENGTH: 30
<212> TYPE: DNA
<213> ORGANISM: Artificial sequence
<220> FEATURE:
<223> OTHER INFORMATION: primers P2 of epoxide hydrolase SpEH

<400> SEQUENCE: 7
cccaagcttt tacaggtcca tctgagcgaa                                    30

<210> SEQ ID NO 8
<211> LENGTH: 28
<212> TYPE: DNA
<213> ORGANISM: Artificial sequence
<220> FEATURE:
<223> OTHER INFORMATION: primers P3 of alcohol dehydrogenase MnADH

<400> SEQUENCE: 8
cgggatccat gaccacaacc gtttccgc                                      28

<210> SEQ ID NO 9
<211> LENGTH: 29
<212> TYPE: DNA
<213> ORGANISM: Artificial sequence
<220> FEATURE:
<223> OTHER INFORMATION: primers P4 of alcohol dehydrogenase MnADH

<400> SEQUENCE: 9
cccaagcttc tagatcgtgg cggtgtcga                                     29

<210> SEQ ID NO 10
<211> LENGTH: 29
<212> TYPE: DNA
<213> ORGANISM: Artificial sequence
<220> FEATURE:
<223> OTHER INFORMATION: primers P5 of omega-transaminase PAKomega-TA

<400> SEQUENCE: 10
gaagatctat gaacagccaa atcaccaac                                     29

<210> SEQ ID NO 11
<211> LENGTH: 29
<212> TYPE: DNA
<213> ORGANISM: Artificial sequence
<220> FEATURE:
<223> OTHER INFORMATION: primers P6 of omega-transaminase PAKomega-TA

<400> SEQUENCE: 11
ccctcgagtc aagccaggac ggcggcggc                                     29

<210> SEQ ID NO 12
<211> LENGTH: 1380
<212> TYPE: DNA
<213> ORGANISM: Artificial sequence
<220> FEATURE:

<223> OTHER INFORMATION: a cvomega-ta gene sequence

<400> SEQUENCE: 12

```
atgcaaaaac aacgcaccac ctcacaatgg cgcgaactgg atgccgcaca ccacctgcac      60
ccgtttaccg acaccgcaag cctgaatcag gccggcgccc gtgttatgac ccgcggcgaa     120
ggtgtgtatc tgtgggattc tgagggtaac aaaattatcg acggcatggc tggtctgtgg     180
tgcgttaatg tcggctatgg tcgtaaagat tttgccgaag cggcccgtcg ccaaatggaa     240
gaactgccgt tctacaacac cttttttcaaa accacgcatc cggcggtggt tgaactgagc     300
agcctgctgg cggaagttac gccggccggc tttgatcgtg tgttctatac caattcaggt     360
tcggaaagcg tggatacgat gatccgcatg gttcgtcgct actgggacgt ccagggcaaa     420
ccggaaaaga aaaccctgat cggtcgttgg aacggctatc atggttctac gattggcggt     480
gcaagtctgg gcggtatgaa atacatgcac gaacagggcg atctgccgat tccgggtatg     540
gcgcatatcg aacaaccgtg gtggtacaaa cacggcaaag atatgacccc ggacgaattt     600
ggtgtcgtgg cagctcgctg gctggaagaa aaaattctgg aaatcggcgc cgataaagtg     660
gcggccttg ttggcgaacc gattcagggt gcgggcggtg tgattgttcc gccggccacc     720
tattggccga aaattgaacg tatctgccgc aaatacgatg ttctgctggt cgcagacgaa     780
gttatttgtg cctttggtcg taccggcgaa tggttcggtc atcagcactt tggcttccaa     840
ccggacctgt ttacggcagc taaaggcctg agttccggtt atctgccgat cggcgccgtc     900
ttcgtgggta acgcgttgc agaaggtctg attgctggcg gtgatttttaa tcatggcttc     960
acctatagcg gtcacccggt ctgtgcggcc gtggcacatg ctaatgtggc agctctgcgt    1020
gacgaaggca tcgtgcagcg cgttaaagat gacattggtc cgtatatgca aaaacgttgg    1080
cgcgaaacgt ttagccgttt cgaacacgtc gatgacgtgc gcggcgttgg tatggtccag    1140
gcatttaccc tggtgaaaaa taaagctaaa cgcgaactgt tccggatttt cggcgaaatt    1200
ggtacgctgt gccgtgacat cttttttccgc aacaatctga ttatgcgtgc cgtgtggtgat    1260
cacattgtta gcgccccgcc gctggttatg acccgcgcag aagtcgacga aatgctggcc    1320
gtggcggaac gctgcctgga agaatttgaa cagaccctga agctcgtgg cctggcgtaa    1380
```

<210> SEQ ID NO 13
<211> LENGTH: 30
<212> TYPE: DNA
<213> ORGANISM: Artificial sequence
<220> FEATURE:
<223> OTHER INFORMATION: primers P7 of omega-transaminase Cvomega-TA

<400> SEQUENCE: 13

```
catgcatcag tcaagatgca aaaacaacgc                                        30
```

<210> SEQ ID NO 14
<211> LENGTH: 23
<212> TYPE: DNA
<213> ORGANISM: Artificial sequence
<220> FEATURE:
<223> OTHER INFORMATION: primers P8 of omega-transaminase Cvomega-TA

<400> SEQUENCE: 14

```
actgcagtct tacgccaggc cac                                               23
```

<210> SEQ ID NO 15
<211> LENGTH: 1362
<212> TYPE: DNA
<213> ORGANISM: Artificial sequence

```
<220> FEATURE:
<223> OTHER INFORMATION: a ppta gene sequence

<400> SEQUENCE: 15
atgagcgtca acaacccgca aacccgtgaa tggcaaaccc tgagcgggga gcatcacctc      60
gcacctttca gtgactacaa gcagctgaag gagaaggggc cgcgcatcat caccaaggcc     120
cagggtgtgc atttgtggga tagcgagggg cacaagatcc tcgacggcat ggccggtcta     180
tggtgcgtgg cggtcggcta cggacgtgaa gagctggtgc aggcggcgga aaaacagatg     240
cgcgagctgc cgtactacaa cctgttcttc cagaccgctc acccgcctgc gctcgagctg     300
gccaaggcga tcaccgacgt ggcgccgaaa ggtatgaccc atgtgttctt caccggctcc     360
ggctccgaag gcaacgacac tgtgctgcgc atggtgcgtc actactgggc gctgaagggc     420
aaaccgcaca gcagaccat catcggccgc atcaacggtt accacggctc caccttcgcc     480
ggtgcatgcc tgggcggtat gagcggcatg cacgagcagg gtggcctgcc gatcccgggc     540
atcgtgcaca tccctcagcc gtactggttc ggcgagggag cgacatgac ccctgacgaa      600
ttcggtgtct gggccgccga gcagttggag aagaagatcc tcgaagtcgg cgaagacaac     660
gtcgcggcct tcatcgccga gccgatccag ggcgctggtg gcgtgatcat cccgccggaa     720
acctactggc cgaaggtgaa ggagatcctc gccaggtacg acatcctgtt cgtcgccgac     780
gaggtgatct gcggcttcgg ccgtaccggc gagtggttcg gctcggacta ctacgacctc     840
aagcccgacc tgatgaccat cgcgaaaggc ctgacctccg gttacatccc catgggcggt     900
gtgatcgtgc gtgacaccgt ggccaaggtg atcagcgaag cggcgacttc caaccacggt     960
ttcacctact ccggccaccc ggtggcggcc gcggtgggcc tggaaaacct gcgcattctg    1020
cgtgacgaga aaattgtcga gaaggcgcgc acggaagcgg caccgtattt gcaaaagcgt    1080
ttgcgcgagc tgcaagacca tccactggtg ggtgaagtgc gcggcctggg catgctggga    1140
gcgatcgagc tggtcaagga caaggcaacc cgcagccgtt acgagggcaa gggcgttggc    1200
atgatctgtc gcaccttctg cttcgagaac ggcctgatca tgcgtgcggt gggtgacacc    1260
atgatcatcg cgccgccgct ggtaatcagc catgcggaga tcgacgaact ggtggaaaag    1320
gcgcgcaagt gcctggacct gacccttgag gcgattcaat aa                       1362

<210> SEQ ID NO 16
<211> LENGTH: 33
<212> TYPE: DNA
<213> ORGANISM: Artificial sequence
<220> FEATURE:
<223> OTHER INFORMATION: primers P9 of transaminase PPTA

<400> SEQUENCE: 16
cgggatccat gagcgtcaac aacccgcaaa ccc                                    33

<210> SEQ ID NO 17
<211> LENGTH: 34
<212> TYPE: DNA
<213> ORGANISM: Artificial sequence
<220> FEATURE:
<223> OTHER INFORMATION: primers P10 of transaminase PPTA

<400> SEQUENCE: 17
cccaagcttt tattgaatcg cctcaagggt cagg                                  34

<210> SEQ ID NO 18
<211> LENGTH: 453
<212> TYPE: PRT
```

-continued

<213> ORGANISM: Artificial sequence
<220> FEATURE:
<223> OTHER INFORMATION: an amino acid sequence of a VFTA

<400> SEQUENCE: 18

```
Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
    370                 375                 380

Lys Asp Lys Ala Ser Lys Thr Pro Phe Asp Gly Asn Leu Ser Val Ser
```

| | | | | |
|---|---|---|---|---|
| 385 | | 390 | 395 | 400 |

Glu Arg Ile Ala Asn Thr Cys Thr Asp Leu Gly Leu Ile Cys Arg Pro
                405                          410                       415

Leu Gly Gln Ser Val Val Leu Cys Pro Pro Phe Ile Leu Thr Glu Ala
                420                          425                       430

Gln Met Asp Glu Met Phe Asp Lys Leu Glu Lys Ala Leu Asp Lys Val
                435                          440                       445

Phe Ala Glu Val Ala
    450

```
<210> SEQ ID NO 19
<211> LENGTH: 40
<212> TYPE: DNA
<213> ORGANISM: Artificial sequence
<220> FEATURE:
<223> OTHER INFORMATION: primers P11 of transaminase VFTA

<400> SEQUENCE: 19
gtcgcggatc cgaattcatg accacaaccc aatctcgcct                           40

<210> SEQ ID NO 20
<211> LENGTH: 32
<212> TYPE: DNA
<213> ORGANISM: Artificial sequence
<220> FEATURE:
<223> OTHER INFORMATION: primers P12 of transaminase VFTA

<400> SEQUENCE: 20
atttcgccgg attcagcgac ccgtttagag gc                                   32

<210> SEQ ID NO 21
<211> LENGTH: 1127
<212> TYPE: DNA
<213> ORGANISM: Artificial sequence
<220> FEATURE:
<223> OTHER INFORMATION: RBS sequence

<400> SEQUENCE: 21
gctctagagg gaggagcaac tcccctaccc tacgctcatt ttcatgacca caaccgtttc     60
cgcctagatc gtggcggtgt cgatcacgaa ccggtaccgc acatcgctgg agagcacgcg    120
gtcccaggcc tcgttgacgt aggacgcctc gatgacctcg atctccgggg tgacgccgtg    180
ttcggcgcag aaatcgagca tctcctgggt ctccgggata ccgccgatca tcgagccgga    240
gatgctgcgt cggccacctg ccagcgggaa gaagggcacc tcgagcggat gctcgggcgc    300
tcccagctcg accagcgtgc catcgatctt gagcagcgag aggtactgac cgagatcgag    360
attggccgat acggtgttca ggatcagatc gaacttgccg ccagcttgc  tgaaggtgtc    420 gggatcgctg gtcgcgtagt actcgtcggc gccgagtcgc aggccgtctt ccatcttctt    480
gagcgactgg ctgagaacgg tcaccttggc gcccatcgcg tgggccagct tgacgcccat    540
gtggccgagc cgccgagtc cgacgattgc gacctccttg ccggggccgg cgttccagtg    600
cttcagcggg gagaacagcg tgatgcccgc gcacagcagg ggagcggcct tgtccagcgg    660
aatgctgtcc gggatgcgca ggacgaactt ttcgtcgacg acgatggcct ggctgtaccc    720
accctgggtg atggtgccgt cccggtcggt ggcgccgtag gtgccgatca tgccggtgcc    780
caggcagtac tgctccaggc ccgccgcgca gttctcgcag ttctggcagg agttcaccat    840
gcagccgacg ccgacgtggt cgccgacctt gtacttggtg acctccgagc cgacctcggt    900
gacgacgccg gcgatctcgt gaccgacgac gagcgggtag ctgggggtgc cccactcggc    960
```

```
cttggcggtg tggatgtcgc tgtgacagat gccggcgaac ttgatgtcga aggccacatc    1020
gtgcgggccg acgtcacggc gctcgatggt ggtcttggcc agcggatctg tcgcggaggt    1080
ggcggcgtag gcggaaacgg ttgtggtcat tccgctacga aactaga                 1127
```

<210> SEQ ID NO 22
<211> LENGTH: 1122
<212> TYPE: DNA
<213> ORGANISM: Artificial sequence
<220> FEATURE:
<223> OTHER INFORMATION: RBS sequence

<400> SEQUENCE: 22

```
gctctagaag gggatccgcc cctcaaatct acggtcctat gaccacaacc gtttccgcct     60
agatcgtggc ggtgtcgatc acgaaccggt accgcacatc gctggagagc acgcggtccc    120
aggcctcgtt gacgtaggac gcctcgatga cctcgatctc cggggtgacg ccgtgttcgg    180
cgcagaaatc gagcatctcc tgggtctccg ggataccgcc gatcatcgag ccggagatgc    240
tgcgtcggcc acctgccagc gggaagaagg gcacctcgag cggatgctcg ggcgctccca    300
gctcgaccag cgtgccatcg atcttgagca gcgagaggta ctgaccgaga tcgagattgg    360
ccgatacggt gttcaggatc agatcgaact tgccggccag cttgctgaag gtgtcgggat    420
cgctggtcgc gtagtactcg tcggcgccga gtcgcaggcc gtcttccatc ttcttgagcg    480
actggctgag aacggtcacc ttggcgccca tcgcgtgggc cagcttgacg cccatgtggc    540
cgaggccgcc gagtccgacg attgcgacct ccttgccggg gccggcgttc cagtgcttca    600
gcggggagaa cagcgtgatg cccgcgcaca gcaggggagc ggccttgtcc agcggaatgc    660
tgtccgggat gcgcaggacg aactttttcgt cgacgacgat ggcctggctg tacccaccct    720
gggtgatggt gccgtcccgg tcggtggcgc cgtaggtgcc gatcatgccg gtgcccaggc    780
agtactgctc caggcccgcc gcgcagttct cgcagttctg gcaggagttc accatgcagc    840
cgacgccgac gtgtcgccg accttgtact tggtgacctc cgagccgacc tcggtgacga    900
cgccggcgat ctcgtgaccg acgacgagcg ggtagctggg ggtgcccac tcggccttgg    960 cggtgtggat gtcgctgtga cagatgccgg cgaacttgat gtcgaaggcc acatcgtgcg    1020
ggccgacgtc acggcgctcg atggtggtct tggccagcgg atctgtcgcg gaggtggcgg    1080
cgtaggcgga aacggttgtg gtcattccgc tacgaaacta ga                     1122
```

<210> SEQ ID NO 23
<211> LENGTH: 1122
<212> TYPE: DNA
<213> ORGANISM: Artificial sequence
<220> FEATURE:
<223> OTHER INFORMATION: RBS sequence

<400> SEQUENCE: 23

```
gctctagaag gggatccgcc cctcaaatct acggtcctat gaccacaacc gtttccgcct     60
agatcgtggc ggtgtcgatc acgaaccggt accgcacatc gctggagagc acgcggtccc    120
aggcctcgtt gacgtaggac gcctcgatga cctcgatctc cggggtgacg ccgtgttcgg    180
cgcagaaatc gagcatctcc tgggtctccg ggataccgcc gatcatcgag ccggagatgc    240
tgcgtcggcc acctgccagc gggaagaagg gcacctcgag cggatgctcg ggcgctccca    300
gctcgaccag cgtgccatcg atcttgagca gcgagaggta ctgaccgaga tcgagattgg    360
ccgatacggt gttcaggatc agatcgaact tgccggccag cttgctgaag gtgtcgggat    420
```

| | |
|---|---:|
| cgctggtcgc gtagtactcg tcggcgccga gtcgcaggcc gtcttccatc ttcttgagcg | 480 |
| actggctgag aacggtcacc ttggcgccca tcgcgtgggc cagcttgacg cccatgtggc | 540 |
| cgaggccgcc gagtccgacg attgcgacct ccttgccggg gccggcgttc cagtgcttca | 600 |
| gcggggagaa cagcgtgatg cccgcgcaca gcagggagc ggccttgtcc agcggaatgc | 660 |
| tgtccgggat gcgcaggacg aacttttcgt cgacgacgat ggcctggctg tacccaccct | 720 |
| gggtgatggt gccgtccgg tcggtggcgc cgtaggtgcc gatcatgccg gtgcccaggc | 780 |
| agtactgctc caggcccgcc gcgcagttct cgcagttctg caggagttc accatgcagc | 840 |
| cgacgccgac gtggtcgccg accttgtact tggtgacctc cgagccgacc tcggtgacga | 900 |
| cgccggcgat ctcgtgaccg acgacgagcg ggtagctggg ggtgcccac tcggccttgg | 960 |
| cggtgtggat gtcgctgtga cagatgccgg cgaacttgat gtcgaaggcc acatcgtgcg | 1020 |
| ggccgacgtc acgcgctcg atggtggtct tggccagcgg atctgtcgcg gaggtggcgg | 1080 |
| cgtaggcgga acggttgtg gtcattccgc tacgaaacta ga | 1122 |

<210> SEQ ID NO 24
<211> LENGTH: 1127
<212> TYPE: DNA
<213> ORGANISM: Artificial sequence
<220> FEATURE:
<223> OTHER INFORMATION: RBS sequence

<400> SEQUENCE: 24

| | |
|---|---:|
| gctctagaga ttacagaaaa cccactctct acgagttatt tatatgacca caaccgtttc | 60 |
| cgcctagatc gtggcggtgt cgatcacgaa ccggtaccgc acatcgctgg agagcacgcg | 120 |
| gtcccaggcc tcgttgacgt aggacgcctc gatgacctcg atctccgggg tgacgccgtg | 180 |
| ttcggcgcag aaatcgagca tctcctgggt ctccgggata ccgccgatca tcgagccgga | 240 |
| gatgctgcgt cggccacctg ccagcgggaa gaagggcacc tcgagcggat gctcgggcgc | 300 |
| tcccagctcg accagcgtgc catcgatctt gagcagcgag aggtactgac cgagatcgag | 360 |
| attggccgat acggtgttca ggatcagatc gaacttgccg gccagcttgc tgaaggtgtc | 420 |
| gggatcgctg gtcgcgtagt actcgtcggc gccgagtcgc aggccgtctt ccatcttctt | 480 |
| gagcgactgg ctgagaacgg tcaccttggc gcccatcgcg tgggccagct tgacgcccat | 540 |
| gtggccgagg ccgccgagtc cgacgattgc gacctccttg ccggggccgg cgttccagtg | 600 |
| cttcagcggg gagaacagcg tgatgcccgc gcacagcagg ggagcggcct tgtccagcgg | 660 |
| aatgctgtcc gggatgcgca ggacgaactt ttcgtcgacg acgatggcct ggctgtaccc | 720 |
| accctgggtg atggtgccgt cccggtcggt ggcgccgtag gtgccgatca tgccggtgcc | 780 |
| caggcagtac tgctccaggc ccgccgcgca gttctcgcag ttctggcagg agttcaccat | 840 |
| gcagccgacg ccgacgtggt cgccgacctt gtacttggtg acctccgagc cgacctcggt | 900 |
| gacgacgccg gcgatctcgt gaccgacgac gagcgggtag ctgggggtgc ccactcggc | 960 |
| cttggcggtg tggatgtcgc tgtgacagat gccggcgaac ttgatgtcga aggccacatc | 1020 |
| gtgcgggccg acgtcacggc gctcgatggt ggtcttggcc agcggatctg tcgcggaggt | 1080 |
| ggcggcgtag gcgaaacgg ttgtggtcat tccgctacga aactaga | 1127 |

<210> SEQ ID NO 25
<211> LENGTH: 63
<212> TYPE: DNA
<213> ORGANISM: Artificial sequence
<220> FEATURE:
<223> OTHER INFORMATION: upstream primers r1

-continued

<400> SEQUENCE: 25
gctctagagg gaggagcaac tcccctaccc tacgctcatt ttcatgacca caaccgtttc    60
cgc    63

<210> SEQ ID NO 26
<211> LENGTH: 56
<212> TYPE: DNA
<213> ORGANISM: Artificial sequence
<220> FEATURE:
<223> OTHER INFORMATION: upstream primers r2

<400> SEQUENCE: 26
gctctagaat cgtctgatct cctacggtta tttttatga ccacaaccgt ttccgc    56

<210> SEQ ID NO 27
<211> LENGTH: 58
<212> TYPE: DNA
<213> ORGANISM: Artificial sequence
<220> FEATURE:
<223> OTHER INFORMATION: upstream primers r3

<400> SEQUENCE: 27
gctctagaag gggatccgcc cctcaaatct acggtcctat gaccacaacc gtttccgc    58

<210> SEQ ID NO 28
<211> LENGTH: 63
<212> TYPE: DNA
<213> ORGANISM: Artificial sequence
<220> FEATURE:
<223> OTHER INFORMATION: upstream primers r4

<400> SEQUENCE: 28
gctctagaga ttacagaaaa cccactctct acgagttatt tatatgacca caaccgtttc    60
cgc    63

<210> SEQ ID NO 29
<211> LENGTH: 48
<212> TYPE: DNA
<213> ORGANISM: Artificial sequence
<220> FEATURE:
<223> OTHER INFORMATION: upstream primers r5

<400> SEQUENCE: 29
gctctagaca cagtctactg ttatttttat gaccacaacc gtttccgc    48

<210> SEQ ID NO 30
<211> LENGTH: 34
<212> TYPE: DNA
<213> ORGANISM: Artificial sequence
<220> FEATURE:
<223> OTHER INFORMATION: downstream primer r6

<400> SEQUENCE: 30
ctagctccaa gcttctagat cgtggcggtg tcga    34

<210> SEQ ID NO 31
<211> LENGTH: 35
<212> TYPE: DNA
<213> ORGANISM: Artificial sequence
<220> FEATURE:
<223> OTHER INFORMATION: downstream primer r7

<400> SEQUENCE: 31

```
caattggcca agcttctaga tcgtggcggt gtcga                              35

<210> SEQ ID NO 32
<211> LENGTH: 36
<212> TYPE: DNA
<213> ORGANISM: Artificial sequence
<220> FEATURE:
<223> OTHER INFORMATION: downstream primer r8

<400> SEQUENCE: 32
ccatatggcc aagcttctag atcgtggcgg tgtcga                             36

<210> SEQ ID NO 33
<211> LENGTH: 35
<212> TYPE: DNA
<213> ORGANISM: Artificial sequence
<220> FEATURE:
<223> OTHER INFORMATION: downstream primer r9

<400> SEQUENCE: 33
atactggcca agcttctaga tcgtggcggt gtcga                              35

<210> SEQ ID NO 34
<211> LENGTH: 36
<212> TYPE: DNA
<213> ORGANISM: Artificial sequence
<220> FEATURE:
<223> OTHER INFORMATION: downstream primer r10

<400> SEQUENCE: 34
cctactggcc aagcttctag atcgtggcgg tgtcga                             36

<210> SEQ ID NO 35
<211> LENGTH: 30
<212> TYPE: DNA
<213> ORGANISM: Artificial sequence
<220> FEATURE:
<223> OTHER INFORMATION: primers P7 of glutamate dehydrogenase

<400> SEQUENCE: 35
gaagatctat ggatcagaca tattctctgg                                    30

<210> SEQ ID NO 36
<211> LENGTH: 30
<212> TYPE: DNA
<213> ORGANISM: Artificial sequence
<220> FEATURE:
<223> OTHER INFORMATION: primers P8 of glutamate dehydrogenase

<400> SEQUENCE: 36
ccctcgagtt aaatcacacc ctgcgccagc                                    30
```

METHOD FOR PRODUCING 1,2-AMINO ALCOHOL COMPOUND BY WHOLE CELL TRANSFORMATION

CROSS-REFERENCE TO RELATED APPLICATION

This application claims priority to Chinese Application No. 201811344825.X filed on Nov. 13, 2018, the entire contents of which are herein incorporated by reference.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created Nov. 13, 2019, is named "Sequence_ST25" and is 30 Kb in size.

TECHNICAL FIELD

The present invention relates to a method for producing a 1,2-amino alcohol compound by utilizing whole-cell transformation, and pertains to the technical field of gene engineering and microorganism engineering.

BACKGROUND

A chiral vicinal amino alcohol compound (1,2-amino alcohol compound) is an important medical intermediate, which not only may be used for synthesizing multiple medicines with physiological activity, such as Randolazine used as anti-anginal inhibitor, Metoprolol used for treating multiple cardiovascular diseases and Nebivolol also used for treating multiple cardiovascular diseases, but also may be as a ligand used for asymmetric synthesis of a chiral catalyst or be used as a chiral building block for synthesizing a chiral compound, as a result, a chiral vicinal amino alcohol compound (1,2-amino alcohol compound) has important application in the fields of medicine, chemical synthesis and the like.

Currently, preparation of a 1,2-amino alcohol compound is mainly implemented by a chemical synthesis method and a biotransformation method. Although a chemical synthesis method is mature in technology, reaction conditions are violent, and many by-products will be generated, sometimes, some organic solvents causing pollution to environment need to be used; in comparison, a biotransformation method is relatively mild in conditions, safe and low in cost, moreover, a 1,2-amino alcohol compound generated by a biotransformation method has the advantages of being high in optical purity, strong in specificity, less in by-products and the like, as a result, preparation of 1,2-amino alcohol compound with a biological method gained wide attention in recent years.

In the aspect of biosynthesis of 1,2-amino alcohol compounds, foreign countries started earlier, in 2006, Iwasaki et al. successfully synthesized (R)-3,4-dimethoxyamphetamine[(R)-DMA] by taking 3,4-dimethoxyphenylacetone as a substrate and (R)-1-phenethylamine as an amino donor by utilizing *Arthrobacter* sp. producing (R)-transaminase in combination with a mode of whole-cell transformation, a transformation rate reaches 82%, and an ee value is greater than 99%, however, the method has the defects of high substrate price, long transformation time (longer than 20 h), generation of by-products and the like; in 2016, Shuke Wu in Korea successfully catalyzed by taking vicinal diol as a substrate by utilizing *Escherichia coli* co-expressing *Pseudomonas putida* Gpo1 sourced alcohol dehydrogenase and *Chromobacterium violaceum* sourced ω-transaminase in combination with a mode of whole-cell transformation to obtain multiple aromatic 1,2-amino alcohol compounds, and the transformation rate reaches more than 65%, however, the method also has the defects of high substrate price, low molar conversion rate, accumulation of intermediate products and the like, and these defects all greatly limit the application of 1,2-amino alcohol compounds.

Therefore, it is necessary to find a steady and efficient method for preparing a 1,2-amino alcohol compound with low cost.

SUMMARY

In order to solve the foregoing problems, the present invention provides an engineered *Escherichia coli* and a method for producing a 1,2-amino alcohol compound by utilizing whole-cell transformation of the engineered *Escherichia coli*. The engineered *Escherichia coli* disclosed by the present invention co-expresses epoxide hydrolase (SpEH), alcohol dehydrogenase (MnADH), ω-transaminase (PAKω-TA) and glutamate dehydrogenase (GluDH), is capable of realizing whole-cell catalysis of an epoxide in one step to synthesize a 1,2-amino alcohol compound, and meanwhile, can realize regeneration of coenzyme $NADP^+$ and an amino doner L-Glu necessary in a process of synthesizing a 1,2-amino alcohol compound; alcohol dehydrogenase (MnADH) expressed by the engineered *Escherichia coli* is RBS optimized alcohol dehydrogenase (MnADH), and such RBS optimization can control the expression quantity of alcohol dehydrogenase, so that the catalysis rate of alcohol dehydrogenase and transaminase can achieve an optimum ratio, to eliminate influence caused by a rate-limiting step in a catalyzing course; by utilizing the method disclosed by the present invention, multiple epoxides (epoxyethylbenzene, epoxypropane, epoxybutane and the like) may be taken as substrates to perform whole-cell transformation to prepare a corresponding 1,2-amino alcohol compound; by utilizing a method disclosed by the present invention to prepare a 1,2-amino alcohol compound, operation is convenient, a substrate is cheap, no cofactor or amino donor needs to added in a transformation process, and therefore, not only is transformation efficiency increased, but also reaction cost is lowered, and the method has an important industrial application value.

The present invention has the following technical effects:

The present invention provides an engineered *Escherichia coli*, wherein the engineered *Escherichia coli* includes recombinant plasmid A, recombinant plasmid B and an expression host; the recombinant plasmid A includes a target gene A and an expression vector; the recombinant plasmid B includes a target gene B, a target gene C and an expression vector; the target gene A is gene encoding epoxide hydrolase (SpEH); the target gene B is gene encoding alcohol dehydrogenase (MnADH); the target gene C is gene encoding ω-transaminase (PAKω-TA); and the expression host is *Escherichia coli*.

In an implementation mode of the present invention, the epoxide hydrolase (SpEH) is sourced from *Sphingomonas* sp. HXN-200.

In an implementation mode of the present invention, a nucleotide sequence of a gene encoding the epoxide hydrolase (SpEH) is as shown in SEQ ID NO.1.

In an implementation mode of the present invention, the alcohol dehydrogenase (MnADH) is sourced from *Mycobacterium neoaurum*.

In an implementation mode of the present invention, a nucleotide sequence of a gene encoding alcohol dehydrogenase (MnADH) is as shown in SEQ ID NO.2.

In an implementation mode of the present invention, the ω-transaminase (PAKω-TA) is sourced from *Pseudomonas aeruginosa* PAK.

In an implementation mode of the present invention, an amino acid sequence of the ω-transaminase (PAKω-TA) is as shown in SEQ ID NO.3.

In an implementation mode of the present invention, an expression vector on the recombinant plasmid A is pACYC-Duet.

In an implementation mode of the present invention, an expression vector on the recombinant plasmid B is pET-Duet.

In an implementation mode of the present invention, the expression host is *E. coli* BL21.

In an implementation mode of the present invention, the alcohol dehydrogenase (MnADH) is optimized by RBS; RBS optimization of alcohol dehydrogenase (MnADH) means that an RBS sequence used for regulating alcohol dehydrogenase (MnADH) and located at the upstream of alcohol dehydrogenase (MnADH) on recombinant plasmid B is substituted; and a nucleotide sequence of a substituted RBS sequence is as shown in SEQ ID NO.4.

In an implementation mode of the present invention, the recombinant plasmid A also comprises a target gene D; the target gene D is gene for encoding glutamate dehydrogenase (GluDH).

In an implementation mode of the present invention, the glutamate dehydrogenase (GluDH) is sourced from *Escherichia coli* BL21.

In an implementation mode of the present invention, a nucleotide sequence of a gene encoding glutamate dehydrogenase (GluDH) is as shown in SEQ ID NO.5.

The present invention provides a method for producing a 1,2-amino alcohol compound, and the method uses the foregoing engineered *Escherichia coli*.

In an implementation mode of the present invention, according to the method, a catalysis system is formed by taking epoxyethylbenzene, epoxypropane, epoxybutane, epichlorohydrin or epoxypentane as a substrate, taking the engineered *Escherichia coli* as a catalyst and adding coenzyme NADP+, amino donor L-Glu and ammonium chloride, reacting for 10-15 h.

The present invention provides application of the foregoing engineered *Escherichia coli* or the foregoing method for producing a 1,2-amino alcohol compound in preparation of a 1,2-amino alcohol compound.

Beneficial Effects:

(1) The engineered *Escherichia coli* of the present invention co-expresses epoxide hydrolase (SpEH), alcohol dehydrogenase (MnADH), ω-transaminase (PAKω-TA) and glutamate dehydrogenase (GluDH), is capable of realizing whole-cell catalysis of an epoxide in one step to synthesize a 1,2-amino alcohol compound, and meanwhile, can realize regeneration of coenzyme $NADP^+$ and an amino doner L-Glu in a process of synthesizing a 1,2-amino alcohol compound;

(2) alcohol dehydrogenase (MnADH) expressed by the engineered *Escherichia coli* of the present invention is RBS optimized alcohol dehydrogenase, and such RBS optimization can control the expression quantity of alcohol dehydrogenase, so that the catalysis rate of alcohol dehydrogenase and transaminase can achieve an optimum ratio, to eliminate influence caused by a rate-limiting step in a catalyzing course (adding IPTG to a culture medium after the engineered *Escherichia coli* of the present invention is cultured to a degree that $OD_{600}$ is 0.8 in the culture medium and inducing for 12 h, so that the enzyme activity of alcohol dehydrogenase in a fermentation broth is up to 0.78 U/mL);

(3) by utilizing a method of the present invention, multiple epoxides (epoxyethylbenzene, epoxypropane, epoxybutane and the like) may be taken as substrates to perform whole-cell transformation to prepare a corresponding 1,2-amino alcohol compound (a product transformation rate may be up to 97.5%); and (4) by utilizing a method disclosed by the present invention to prepare a 1,2-amino alcohol compound, operation is convenient, a substrate is cheap, no cofactor or amino donor needs to added in a transformation process, and therefore, not only is transformation efficiency increased, but also reaction cost is lowered, and the method has an important industrial application value.

DETAILED DESCRIPTION

Further descriptions will be made to the present invention below in combination with specific embodiments.

*E. coli* BL21 competent cell involved in the following embodiments is purchased from Shanghai Sangon Biotech Co., Ltd.

Detection method involved in the following embodiments are as follows:

An SpEH Enzyme Activity Determination Method:

1 mL of a reaction system includes 150 μL of 10 mM epoxyethylbenzene and 50 μL of enzyme solution;

enzyme activity definition: enzyme amount for generating phenyl 1,2-glycol by transforming 1 μmol of epoxyethylbenzene for 1 min at 37° C. is defined as one enzyme activity unit (U).

A PAKω-TA Enzyme Activity Determination Method:

1 mL of a reaction system includes 150 μL of 10 mM epoxyethylbenzene and 50 μL of enzyme solution;

enzyme activity definition: enzyme amount for generating 2-amino1-phenethyl alcohol by transforming 1 μmol of hydroxyl phenylacetaldehyde for 1 min at 37° C. is defined as one enzyme activity unit (U).

An MnADH Enzyme Activity Determination Method:

1 mL of a reaction system includes 790 μL of 50 mM phosphate buffer solution (pH 8.0), 150 μL of 10 mM phenyl 1,2-glycol, 10 μL of 1 μmol NADP+ and 50 μL of enzyme solution;

after reaction is ended, determining activity according to NADPH light absorption value variation of a reaction solution in 340 nm;

enzyme activity definition: enzyme amount needed for generating 1 μmol of NADPH in 1 min.

A GluDH Enzyme Activity Determination Method:

1 mL of a reaction system includes 790 μL of 50 mM phosphate buffer solution (pH 8.0), 150 μL of 10 mM 2-oxoglutaric acid, 10 μL of 1 μmol NADPH and 50 μL of enzyme solution;

after reaction is ended, determining activity according to NADPH light absorption value variation of a reaction solution in 340 nm;

enzyme activity definition: enzyme amount needed for generating 1 μmol of NADPH in 1 min.

An Epoxide Consumption Determination Method:

Chromatographic conditions: a chromatographic column: DinosoilC18 (5 μL, 250 nm×4.6 nm), a mobile phase:

acetonitrile-water (V/V=85:15), column temperature: 30° C., a sample size: 10 μL, a flow rate: 1.0 mL/min.

After chromatography is ended, detecting a characteristic absorption peak at 220 nm ultraviolet wavelength, wherein the concentration of a substrate standard sample is 0.5 g/L.

A 1,2-Amino Alcohol Compound Yield Determination Method:

Chromatographic conditions: a chromatographic column: DinosoilC18 (5 μL, 250 nm×4.6 nm), a mobile phase: acetonitrile-water (V/V=85:15), column temperature: 30° C., a sample size: 10 μL, a flow rate: 1.0 mL/min.

After chromatography is ended, detecting a characteristic absorption peak at 220 nm ultraviolet wavelength, wherein the concentration of a product standard sample is 0.5 g/L.

A Determination Method of Intermediate Product Vicinal Diol and 1,2-Amino Alcohol Compound Chromatographic conditions: a chromatographic column: Sepax Carbomix H-NP (10:8, 7.8 mm*300 mm), a mobile phase: 3 mM perchloric acid solution, column temperature: 50° C., a sample size: 10 μL, a flow rate: 1.0 mL/min.

After chromatography is ended, detecting a characteristic absorption peak at 3380 nm ultraviolet wavelength, wherein the concentration of an intermediate product standard sample is 0.5 g/L.

Culture media involved in the following embodiments are as follows:

An LB solid culture medium: 10 g/L of peptone, 5 g/L of yeast extract, 10 g/L of NaCl, 0.2 g/L of agar powder.

An LB liquid culture medium: 10 g/L of peptone, 5 g/L of yeast extract, 10 g/L of NaCl.

Embodiment 1: Construction of Recombinant Plasmid

Specific steps are as follows:

(1) design PCR primers P1 and P2 (SEQ ID NO.6 and SEQ ID NO.7) of epoxide hydrolase SpEH according to a speh gene sequence (SEQ ID NO.1) in a whole genome nucleotide sequence of *Sphingomonas* sp. HXN-200 in NCBI;

(2) design PCR primers P3 and P4 (SEQ ID NO.8 and SEQ ID NO.9) of alcohol dehydrogenase MnADH according to a mnadh gene sequence (SEQ ID NO.2) in a whole genome nucleotide sequence of *Mycobacterium neoaurum* in NCBI;

(3) design PCR primers P5 and P6 (SEQ ID NO.10 and SEQ ID NO.11) of ω-transaminase PAKω-TA according to a pakω-ta gene sequence (an amino acid sequence being SEQ ID NO.3) in a whole genome nucleotide sequence of *Pseudomonas aeruginosa* PAK in NCBI;

(4) design PCR primers P7 and P8 (SEQ ID NO.13 and SEQ ID NO.14) of ω-transaminase Cvω-TA according to a cvω-ta gene sequence (SEQ ID NO.12) in a whole genome nucleotide sequence of *Chromobacterium violaceum* in NCBI;

(5) design PCR primers P9 and P10 (SEQ ID NO.16 and SEQ ID NO.17) of transaminase PPTA according to a ppta gene sequence (SEQ ID NO.15) in a whole genome nucleotide sequence of *Pseudomonas putida* in NCBI;

(6) design PCR primers P11 and P12 (SEQ ID NO.19 and SEQ ID NO.20) of transaminase VFTA according to a vfta gene sequence (an amino acid sequence is as shown in SEQ ID NO.18) in a whole genome nucleotide sequence of *Vibrio fluvialis* in NCBI;

(7) perform PCR amplification by utilizing the foregoing primers by taking the foregoing genome DNA as a template, amplification conditions being: initial denaturation at 95° C. for 5 min, one cycle; denaturation at 95° C. for 1 min, annealing at 58° C. for 1 min, extension at 72° C. for 1 min 30 s, 30 cycles; final extension at 72° C. for 10 min, and after amplification is ended, purify and recycle PCR products by adopting a gel extraction kit; and (8) connect recycling products speh and pACYCDuet by PCR after digestion with BamH I and Hind II, connect mnadh, pakω-ta and pETDuet by PCR after digestion with BamH I/Hind III and Bgl II/EcoR V respectively, connect mnadh, cvω-ta and pETDuet by PCR after digestion with BamH I/Hind III and Bgl II/EcoR V respectively, connect mnadh, ppta and pETDuet by PCR after digestion with BamH I/Hind III and Bgl II/EcoR V respectively, and connect mnadh, vfta and pETDuet by PCR after digestion with amH I/Hind III and Bgl II/EcoR V respectively, to obtain recombinant plasmids pACYCDuet-speh, pETDuet-mnadh-pakω-ta, pETDuet-mnadh-cvω-ta, pETDuet-mnadh-ppta, pETDuet-mnadh-vfta.

Embodiment 2: Construction of Recombinant Bacteria

Specific steps are as follows:

Put 100 μL of *E. coli* BL21 competent cell into a 1.5 mL centrifugal tube, respectively add 5 μL of recombinant plasmids pACYCDuet-speh and pETDuet-mnadh-pakω-ta, pACYCDuet-speh and pETDuet-mnadh-cvω-ta, pACYCDuet-speh and pETDuet-mnadh-ppta, pACYCDuet-speh and pETDuet-mnadh-vfta needing transformation, blow and suck gently, place on ice for 45 min; perform precise heat shock on the centrifugal tube at 42° C. for 90 s, then place on ice again for 5 min, then add 800 μL of LB liquid culture medium, perform shake cultivation for 1-1.5 h at 37° C.; remove most supernatant after centrifugation, block and suck again for suspension, coat residual bacteria solution to an LB dish with ampicillin resistance and chlorampenicol resistance, and extract plasmids for verification after transformants come out, to obtain recombinant plasmids BL21/pACYCDuet-speh&pETDuet-mnadh-pakω-ta, BL21/pACYCDuet-speh&pETDuet-mnadh-cvω-ta, BL21/pACYCDuet-speh&pETDuet-mnadh-ppta and BL21/pACYCDuet-speh&pETDuet-mnadh-vfta.

Embodiment 3: Verification of Recombinant Bacteria

Specific steps are as follows:

(1) activate recombinant plasmids BL21/pACYCDuet-speh&pETDuet-mnadh-pakω-ta, BL21/pACYCDuet-speh&pETDuet-mnadh-cvω-ta, BL21/pACYCDuet-speh&pETDuet-mnadh-ppta and BL21/pACYCDuet-speh&pETDuet-mnadh-vfta obtained in embodiment 2 with an LB culture medium and then culture for 12 h in the conditions of 37° C., 160 r/min, to obtain a seed solution;

(2) inoculate the seed solution to 100 mL of LB liquid culture medium at an inoculation amount of 1%, and continue to culture for 2 h until $OD_{600}$ is 0.8, to obtain a fermentation broth;

(3) add IPTG with final concentration of 0.8 mM to the fermentation broth, induce for 12 h at 28° C., centrifuge for 10 min in the conditions of 4° C., 8000 r/min and collect thalli;

(4) rinse the thalli with a phosphate buffer solution with pH of 7.5 for two times, then add the thalli into a catalysis system and react for 10 h at 37° C. to obtain a reaction solution, wherein $OD_{600}$ of the thalli in the catalysis system is equal to 30, besides thalli, the catalysis system also contains 100 mM of substrate epoxyethylbenzene, 5 mM of L-Glu, 0.02 mM of NADP+, 0.35 mM of PLP and 275 mM of NH$_4$Cl (pH 8.0); and (5) dilute the reaction solution and filter with a 0.22 μm filter membrane and then perform HPLC analysis.

An HPLC analysis result shows that: after whole-cell transformation of 100 mM of epoxyethylbenzene with recombinant bacteria BL21/pACYCDuet-speh&pETDuet-mnadh-pakω-ta for 10 h, the amount of a product, 2-amino1-phenethyl alcohol, is 22.4 mM, the accumulation amount of an intermediate product, phenyl 1,2-glycol, is 76.5 mM, and another intermediate product, hydroxyl phenylacetaldehyde, is not accumulated;

after whole-cell transformation of 100 mM of epoxyethylbenzene with recombinant bacteria BL21/pACYCDuet-speh&pETDuet-mnadh-cvω-ta for 10 h, the amount of a product, 2-amino1-phenethyl alcohol, is 10.2 mM, the accumulation amount of an intermediate product, phenyl 1,2-glycol, is 78.4 mM, and the accumulation amount of another intermediate product, hydroxyl phenylacetaldehyde, is 11.2 mM;

after whole-cell transformation of 100 mM of epoxyethylbenzene with recombinant bacteria BL21/pACYCDuet-speh&pETDuet-mnadh-ppta for 10 h, the amount of a product, 2-amino1-phenethyl alcohol, is 0 mM, the accumulation amount of an intermediate product, phenyl 1,2-glycol, is 82 mM, and the accumulation amount of another intermediate product, hydroxyl phenylacetaldehyde, is 16.5 mM; and after whole-cell transformation of 100 mM of epoxyethylbenzene with recombinant bacteria BL21/pACYCDuet-speh&pETDuet-mnadh-vfta for 10 h, the amount of a product, 2-amino1-phenethyl alcohol, is 3.5 mM, the accumulation amount of an intermediate product, phenyl 1,2-glycol, is 80.2 mM, and the accumulation amount of another intermediate product, hydroxyl phenylacetaldehyde, is 13.6 mM;

It is known from a result that: when trying to use four kinds of ω-transaminase from different sources, the yield of ω-transaminase sourcing from *Pseudomonas aeruginosa* PAK is the highest, indicating that PAKω-TA enzyme activity is higher than the enzyme activity of enzyme from the other three sources, as a result, ω-transaminase PAKω-TA should be selected to construct recombinant bacteria.

Furthermore, it found, by detecting the content of intermediate products, phenyl 1,2-glycol and hydroxyl phenylacetaldehyde, in a catalysis reaction process, that a large amount of intermediate product phenyl 1,2-glycol is accumulated, hydroxyl phenylacetaldehyde is not accumulated, while the action of alcohol dehydrogenase MnADH in a whole catalysis system is to catalyze intermediate product phenyl 1,2-glycol to synthesize hydroxyl phenylacetaldehyde, and the action of ω-transaminase PAKω-TA is to catalyze hydroxyl phenylacetaldehyde to synthesize a final product 2-amino1-phenethyl alcohol; when a crude enzyme solution of alcohol dehydrogenase MnADH is added from the outside, intermediate product phenyl 1,2-glycol may be gradually consumed and finally be totally transformed to be the final product 2-amino1-phenethyl alcohol, in a whole catalysis process, intermediate product hydroxyl phenylacetaldehyde is not accumulated, and the result shows that preparation of a 1,2-amino alcohol compound by transformation of recombinant bacteria BL21/pACYCDuet-speh&pETDuet-mnadh-pakω-ta will be limited by relatively low enzyme activity of alcohol dehydrogenase, while the transformation rate of other enzymes is not limited, finally resulting in massive accumulation of intermediate products and relatively low yield of a final product, as a result, it still needs to further improve the enzyme activity of alcohol dehydrogenase in a whole tandem catalysis system.

Embodiment 4: RBS Sequence Optimization of Alcohol Dehydrogenase

Specific steps are as follows:

(1) design PCR upstream primers r1, r2, r3, r4, r5 (sequences being as shown in SEQ ID NO: 25-SEQ ID NO: 29) containing RBS sequences (sequences being as shown in SEQ ID NO: 4, SEQ ID NO: 21-SEQ ID NO: 24) of different intensities according to a T7 promotor on pETDuet plasmid and a gene sequence of MnADH;

(2) constitute primer pairs from upstream primers r1, r2, r3, r4, r5 containing RBS sequences of different intensities and downstream primer r6, r7, r8, r9, r10 (sequences being as shown in SEQ ID NO: 30-SEQ ID NO: 34) by taking recombinant plasmid pETDuet-mnadh-pakω-ta as a template, perform PCR to obtain multiple segments of an alcohol dehydrogenase gene containing RBS sequences of different intensities, connect the segments with linearized pETDuet-pakω-ta, to obtain co-expression plasmids pETDuet-r1-mnadh-pakω-ta, pETDuet-r2-mnadh-pakω-ta, pETDuet-r3-mnadh-pakω-ta, pETDuet-r4-mnadh-pakω-ta, pETDuet-r5-mnadh-pakω-ta with different RBS intensities;

(3) transform recombinant plasmids into competent *E. coli* BL21, and screen correct transformants, to obtain co-expression recombinant bacteria after different RBS optimization of alcohol dehydrogenase;

(4) perform induced expression on constructed recombinant bacteria according to conditions in embodiment 3, then collect and wash, and then re-suspend recombinant *Escherichia coli* to 10 mL of 50 mM phosphate buffer solution; and (5) perform ultrasonic disruption on suspended cells, stopping for 3 s after disrupting for 1 s, working for 15 min, put a disruption solution into a centrifugal machine, centrifuge for 25 min at a rate of 10000 r/min at 4° C. to remove precipitates, and measure MnADH enzyme activity in a supernatant.

It is known from a result that: enzyme activity of MnADH in recombinant bacteria pETDuet-r1-mnadh-pakω-ta, pETDuet-r2-mnadh-pakω-ta, pETDuet-r3-mnadh-pakω-ta, pETDuet-r4-mnadh-pakω-ta, pETDuet-r5-mnadh-pakω-ta is respectively 0.78 U/mL, 0.58 U/mL, 0.52 U/mL, 0.43 U/mL, 0.38 U/mL, which is improved to a certain extent in comparison with original bacterium pETDuet-mnadh-pakω-ta without RBS optimization (enzyme activity of MnADH of an original bacterium is 0.32 U/mL).

Therefore, an RBS sequence with sequence of SEQ ID NO: 4 should be selected to optimize alcohol dehydrogenase.

Embodiment 5: Introduction of Glutamate Dehydrogenase

It is found from the foregoing experiments that coenzyme NADP+ and amino donor L-Glu need to be continuously provided for a three-enzyme catalysis system, while introduction of glutamate dehydrogenase may regenerate NADP and L-Glu consumed by a reaction system, and therefore, an attempt may be made to introduction of glutamate dehydrogenase, with specific steps as follows:

(1) design PCR primers P7 and P8 (SEQ ID NO.35 and SEQ ID NO.36) of glutamate dehydrogenase according to gludh gene sequence (SEQ ID NO.5) in a whole genome nucleotide sequence of *Escherichia coli* Bl21 in NCBI;

(2) perform PCR amplification by utilizing the foregoing primers by taking the foregoing genome DNA as a template, and connect a recycling product and pACYCDuet-speh by PCR after digestion with Nde I and EcoR, to obtain recombinant plasmid pACYCDuet-speh-gludh;

(3) transform recombinant plasmid pACYCDuet-speh-gludh and recombinant plasmid pETDuet-r1-mnadh-pakω-ta after RBS sequence optimization into competent *E. coli* BL21 at the same time, and if verification is correct, obtain recombinant bacterium *E. coli* BL21 (SGMP) capable of co-expressing four enzymes;

(4) activate obtained recombinant bacterium *E. coli* BL21 (SGMP) with an LB culture medium and then culture for 12 h in the conditions of 37° C., 160 r/min to obtain a seed solution;

(5) inoculate the seed solution to 100 mL of LB liquid culture medium at an inoculation amount of 1%, and continue to culture for 2 h until $OD_{600}$ is 0.8, to obtain a fermentation broth;

(6) add IPTG with final concentration of 0.8 mM to the fermentation broth, induce for 12 h at 28° C., centrifuge for 10 min in the conditions of 4° C., 8000 r/min and collect thalli;

(7) rinse the thalli with a phosphate buffer solution with pH of 7.5 for two times, then add the thalli into a catalysis system and react for 10 h at 37° C. to obtain a reaction solution, wherein $OD_{600}$ of the thalli in the catalysis system is equal to 30, besides thalli, the catalysis system also contains 100 mM of substrate epoxyethylbenzene, 5 mM of L-Glu, 0.02 mM of $NADP^+$, 0.35 mM of PLP and 275 mM of $NH_4Cl$ (pH 8.0); and (8) dilute the reaction solution and filter with a 0.22 µm filter membrane and then perform HPLC analysis.

An HPLC analysis result shows that: after whole-cell transformation of 100 mM of epoxyethylbenzene with recombinant bacteria for 10 h, the amount of a product, 2-amino1-phenethyl alcohol, is 96.5 mM, without accumulation of intermediate products and generation of by-product 2-oxoglutaric acid.

It is known from a result that recombinant bacterium *E. coli* BL21 (SGMP) may be efficiently transformed to prepare a 1,2-amino alcohol compound, and coenzyme and amino donor do not need to be continuously added in the whole reaction process.

Embodiment 6: Four-enzyme Tandem Co-expression

Specific steps are as follows:

(1) connect the foregoing recycling products speh and gludh with pETDuet-r1-mnadh-pakω-ta by PCR respectively after digestion with Kpn I/Xho I and Nde I/EcoR V, to obtain recombinant plasmid pETDuet-r1-mnadh-pakω-ta-speh-gludh;

(2) transform pETDuet-r1-mnadh-pakω-ta-speh-gludh into competent *E. coli* BL21, and if verification is correct, obtain recombinant bacterium *E. coli* BL21/pETDuet-r1-mnadh-pakω-ta-speh-gludh with four enzymes expressed on a same plasmid in a tandem mode;

(3) referring to embodiment 5, transform 100 mM of substrate epoxyethylbenzene by using *E. coli* BL21/pETDuet-r1-mnadh-pakω-ta-speh-gludh; and (4) dilute a reaction solution and filter with a 0.22 µm filter membrane and then perform HPLC analysis.

An HPLC analysis result shows that: after whole-cell transformation of 100 mM of epoxyethylbenzene with recombinant bacteria *E. coli* BL21/pETDuet-r1-mnadh-pakω-ta-speh-gludh for 10 h, the amount of a product, 2-amino1-phenethyl alcohol, is 50.6 mM, and intermediate products phenyl 1,2-glycol (24 mM) and hydroxyl phenylacetaldehyde (14.5 mM) are accumulated.

It is known from a result that co-expression of four enzymes on a same plasmid will be limited by unbalance of expression level of each enzyme, and therefore, it is of great importance to select suitable expression plasmids to achieve an optimum adaption relation.

Embodiment 7: Application of Recombinant Bacteria

Specific steps are as follows:

Taking epoxypropane as a substrate: activate recombinant bacterium *E. coli* BL21 (SGMP) obtained in embodiment 5 with an LB culture medium and then culture for 12 h in the conditions of 37° C., 160 r/min, to obtain a seed solution; inoculate the seed solution to 100 mL of LB liquid culture medium at an inoculation amount of 1%, and continue to culture for 2 h until $OD_{600}$ is 0.8, to obtain a fermentation broth; add IPTG with final concentration of 0.8 mM to the fermentation broth, induce for 12 h at 28° C., centrifuge for 10 min in the conditions of 4° C., 8000 r/min and collect thalli; rinse the thalli with a phosphate buffer solution with pH of 7.5 for two times, then add the thalli into a catalysis system and react for 10 h at 37° C. to obtain a reaction solution, wherein $OD_{600}$ of the thalli in the catalysis system is equal to 30, besides thalli, the catalysis system also contains 100 mM of substrate epoxypropane, 5 mM of L-Glu, 0.02 mM of $NADP^+$, 0.35 mM of PLP and 275 mM of $NH_4Cl$ (pH 8.0); and dilute the reaction solution and filter with a 0.22 µm filter membrane and then perform HPLC analysis.

Taking epoxybutane as a substrate: activate recombinant bacterium *E. coli* BL21 (SGMP) obtained in embodiment 5 with an LB culture medium and then culture for 12 h in the conditions of 37° C., 160 r/min, to obtain a seed solution; inoculate the seed solution to 100 mL of LB liquid culture medium at an inoculation amount of 1%, and continue to culture for 2 h until $OD_{600}$ is 0.8, to obtain a fermentation broth; add IPTG with final concentration of 0.8 mM to the fermentation broth, induce for 12 h at 28° C., centrifuge for 10 min in the conditions of 4° C., 8000 r/min and collect thalli; rinse the thalli with a phosphate buffer solution with pH of 7.5 for two times, then add the thalli into a catalysis system and react for 10 h at 37° C. to obtain a reaction solution, wherein $OD_{600}$ of the thalli in the catalysis system is equal to 30, besides thalli, the catalysis system also contains 100 mM of substrate epoxybutane, 5 mM of L-Glu, 0.02 mM of $NADP^+$, 0.35 mM of PLP and 275 mM of $NH_4Cl$ (pH 8.0); and dilute the reaction solution and filter with a 0.22 µm filter membrane and then perform HPLC analysis.

An HPLC analysis result shows that: after whole-cell transformation of 100 mM of epoxypropane with recombinant bacteria 10 h, the amount of a product, 2-amino1-phenethyl alcohol, is 94.3 mM, after whole-cell transformation of 100 mM of epoxybutane with recombinant bacteria 10 h, the amount of a product, 2-amino1-phenethyl alcohol, is 97.5 mM, and the molar yield of corresponding generated 1,2-amino alcohol compound respectively achieve 94.3% and 97.5%.

Although the present disclosure has been disclosed above through the preferred embodiments, the embodiments are not intended to limit the present disclosure, a person skilled in the art can make various variations and modifications without departing from the spirit and scope of the present invention, therefore, the protection scope of the present invention should be subject to the appended claims.

The present invention discloses a method for producing a 1,2-amino alcohol compound by utilizing whole-cell transformation, and belongs to the technical field of gene engineering and microorganism engineering. According to the present invention, engineered *Escherichia coli* co-expresses epoxide hydrolase, alcohol dehydrogenase, ω-transaminase and glutamate dehydrogenase, is capable of realizing whole-cell catalysis of an epoxide in one step to synthesize a 1,2-amino alcohol compound, and meanwhile, can realize regeneration of coenzyme $NADP^+$ and an amino donor L-Glu; alcohol dehydrogenase expressed by the engineered *Escherichia coli* is RBS optimized alcohol dehydrogenase, and such RBS optimization can control the expression quantity of alcohol dehydrogenase, so that the catalysis rate of alcohol dehydrogenase and transaminase can achieve an optimum ratio, to eliminate influence caused by a rate-limiting step in a catalyzing course; by utilizing the method disclosed by the present invention, multiple epoxides may be taken as substrates to perform whole-cell transformation to prepare a corresponding 1,2-amino alcohol compound, and therefore, the method has an important industrial application value.

What is claimed is:

1. An engineered *Escherichia coli*, wherein the engineered *Escherichia coli* comprises recombinant plasmid A and recombinant plasmid B; the recombinant plasmid A comprising a target gene A and an expression vector; the recombinant plasmid B comprising a target gene B, a target gene C, and an expression vector; the target gene A being a gene encoding epoxide hydrolase (SpEH) comprising SEQ ID NO: 1; the target gene B being a gene encoding alcohol dehydrogenase (MnADH) comprising SEQ ID NO: 2; the target gene C being a gene encoding w-transaminase (PAKω-TA), wherein the amino acid sequence expressed by target gene C comprises SEQ ID NO: 3; and wherein the recombinant plasmid A also comprises a target gene D; the target gene D being a gene encoding glutamate dehydrogenase (GluDH) comprising SEQ ID NO: 5.

2. The engineered *Escherichia coli* according to claim 1, wherein the alcohol dehydrogenase (MnADH) is optimized by RBS; RBS optimization of alcohol dehydrogenase (MnADH) meaning that an RBS sequence used for regulating alcohol dehydrogenase (MnADH) and located at the upstream of alcohol dehydrogenase (MnADH) on recombinant plasmid B is substituted; the substituted RBS sequence comprising SEQ ID NO: 4.

3. A method for producing a 1,2-amino alcohol compound, wherein the method uses the engineered *Escherichia coli* described in claim 1.

4. A method for producing a 1,2-amino alcohol compound, the method comprising:
providing a catalysis system comprising a substrate selected from epoxyethylbenzene, epoxypropane, epoxybutane, epichlorohydrin or epoxypentane and the engineered *Escherichia coli* according to claim 1,
adding coenzyme NADP+, amino donor L-Glu, and ammonium chloride, and
reacting for 10-15 hours.

\* \* \* \* \*